US00PP20805P3

(12) United States Plant Patent

Bak et al.

(10) Patent No.: US PP20,805 P3

(45) Date of Patent: Mar. 2, 2010

(54) *GUZMANIA* PLANT NAMED 'AROSA'

(50) Latin Name: *Guzmania hybrida*
Varietal Denomination: AROSA

(75) Inventors: Elly Bak, Rijsenhout (NL); Nicolaas D. M. Steur, Oude Niedorp (NL)

(73) Assignee: Corn.Bak B.V., Assendelft (NL)

( * ) Notice: Subject to any disclaimer, the term of this patent is extended or adjusted under 35 U.S.C. 154(b) by 0 days.

(21) Appl. No.: 12/315,020

(22) Filed: Nov. 25, 2008

(65) Prior Publication Data

US 2009/0144871 P1 Jun. 4, 2009

(51) Int. Cl.
*A01H 5/00* (2006.01)

(52) U.S. Cl. ..... Plt./371

(58) Field of Classification Search ..... Plt./371
See application file for complete search history.

*Primary Examiner*—Kent L Bell
(74) *Attorney, Agent, or Firm*—Foley & Lardner LLP

(57) ABSTRACT

A new and distinct *Guzmania* hybrid plant named 'AROSA' characterized by solid growth habit; funnel-form rosette plant, measuring about 45 cm in height (above the pot when flowering); numerous, green color foliage, measuring about 50 cm in length and about 3.5 cm to 4.5 cm in width; superior floral bract production; bracts have a unique, compound red-purple inflorescence which distinguishes this cultivar from typical *Guzmania;* compound inflorescence, measuring about 11 cm in height and about 11 cm in diameter; and long-lasting habit.

2 Drawing Sheets

Latin name of the genus and species of the claimed plant: *Guzmania hybrida*

Variety denomination: 'AROSA'.

BACKGROUND OF THE INVENTION

The present invention relates to a new and distinct hybrid cultivar of *Guzmania* plant, botanically known as *Guzmania hybrida*, of the family *Bromeliaceae*, and hereinafter referred to as 'AROSA'.

*Guzmania* is native to tropical America. *Guzmania* is predominantly epiphytic with a few terrestrial species and is native to the tropics. For the most part, species vary in diameter from 7 or 8 inches to 3 or 4 feet and have rosettes of glossy, smooth-edged leaves. Floral bracts of *Guzmania* frequently have brilliant colors and may last for many months. The range of colors for *Guzmania* is generally from yellow through orange but may also include flame red and red-purple. White or yellow, tubular, three-petalled flowers may also appear on a stem or within the leaf rosette but are usually short-lived. *Guzmania* may be advantageously grown as pot plants for greenhouse or home use. Typically, the plants are shaded from direct sunlight. During the spring to autumn period, the central vase-like part of the leaf rosette is normally filled with water.

The new *Guzmania* 'AROSA' originated from a cross made in a controlled breeding program by the inventors in 1997. The female or seed parent is the *Guzmania* hybrid identified by code 973018393 (unpatented). The male or pollen parent is the *Guzmania albo-rosea* cultivar identified by code 97301017 (unpatented). The new *Guzmania* 'AROSA' was discovered and selected by the inventors in 2000 as a single flowering plant within the progeny of the stated cross in a controlled environment in Assendelft, The Netherlands.

Asexual reproduction of the new *Guzmania* cultivar was first performed by off-shoots beginning in 2001 and then by tissue culture beginning in 2003 in Assendelft, The Netherlands, with first flowering after asexual reproduction occurring in 2007 in Assendelft, The Netherlands. Asexual reproduction of the *Guzmania* 'AROSA' has demonstrated that the combination of characteristics as herein disclosed for the new cultivar are firmly fixed and retained through successive generations of asexual reproduction. The new cultivar reproduces true to type.

Methods for cultivation and crossing of *Guzmania* are well known. For a detailed discussion, reference is made to the following publications, which are incorporated herein by reference: Benzing, David H., THE BIOLOGY OF THE BROMELIADS, Mad River Press, Inc., Eureka (1980); Zimmer, Karl, BROMELIEN, Verlag, Paul Parey, Berlin (1986); and Rauh, Werner, BROMELIEN, Verlag Eugen Ulmer, Stuttgart (1981).

BRIEF SUMMARY OF THE INVENTION

The following traits have been repeatedly observed and are determined to be unique characteristics of 'AROSA' which in combination distinguish this *Guzmania* as a new and distinct cultivar:

1. Solid growth habit;
2. Funnel-form rosette plant, measuring about 45 cm in height (above the pot when flowering);
3. Numerous, green color foliage, measuring about 50 cm in length and about 3.5 cm to 4.5 cm in width;
4. Superior floral bract production;
5. Bracts have a unique, compound red-purple inflorescence (RHS 61A) which distinguishes this cultivar from typical *Guzmania*;
6. Compound inflorescence, measuring about 11 cm in height and about 11 cm in diameter; and
7. Long-lasting habit.

Plants of the parental cultivars, *Guzmania* hybrid identified by code 973018393 *Guzmania albo-rosea* cultivar identified by code 97301017 (both unpatented) (unpatented) are no longer available to provide a detailed botanical comparison with the new *Guzmania* hybrid 'AROSA'

Of the many commercial cultivars known to the present inventors, the most similar in comparison to the new *Guzmania* hybrid 'AROSA' is the *Guzmania* cultivar 'TORCH' (patented, U.S. Plant Pat. No. 9,426). Plants of the new hybrid 'AROSA' differ from plants of 'TORCH' primarily in the following characteristics:

1. Plants of 'AROSA' produce compound inflorescence which are red-purple (closest to RHS 61A) in color and measure at maturity about 11 cm in length and about 11 cm in diameter whereas plants of 'TORCH' produce single inflorescence which are bright red (closest to RHS 44A) in color and measure at maturity about 18 cm in length and about 8 cm in width;
2. Plants of 'AROSA' produce leaves that measure about 50 cm in length and about 3.5 to 4.5 cm in width whereas plants of 'TORCH' produce leaves that measure about 37 cm in length and about 5 cm in width; and
3. Plant of 'AROSA' bloom for a whole year about 14 weeks after natural induction or through induction with acetylene whereas plants of 'TORCH' bloom for a whole year about 16 weeks after natural induction or through treatment with acetylene.

BRIEF DESCRIPTION OF THE PHOTOGRAPHS

The accompanying photographs illustrate the overall appearance of the new *Guzmania* hybrid 'AROSA' showing the colors as true as is reasonably possible with colored reproductions of this type. Colors in the photographs may differ slightly from the color values cited in the detailed botanical description which accurately describes the color of 'AROSA'.

DETAILED BOTANICAL DESCRIPTION

Figure 1:
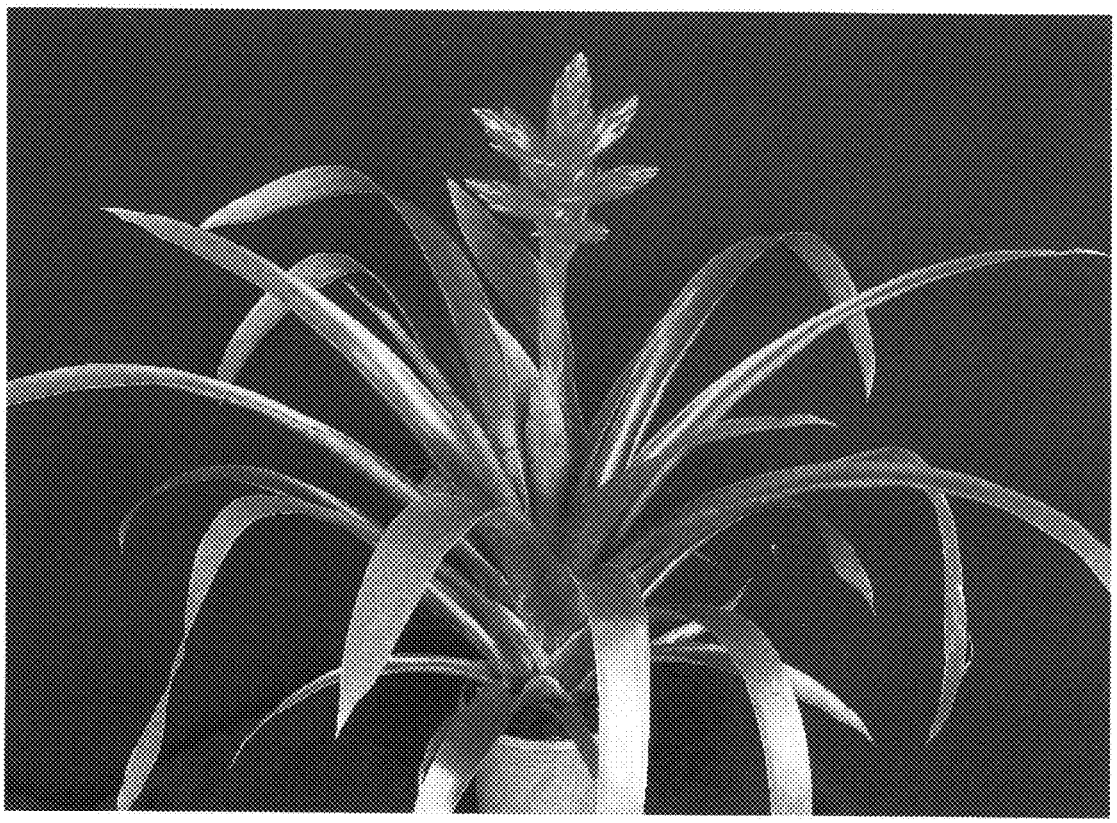
FIG. 1 shows a side view perspective of the primary and top bracts produced by a typical potted, flowering plant of 'AROSA', at 15 months of age in a 12 cm pot.
Figure 2:
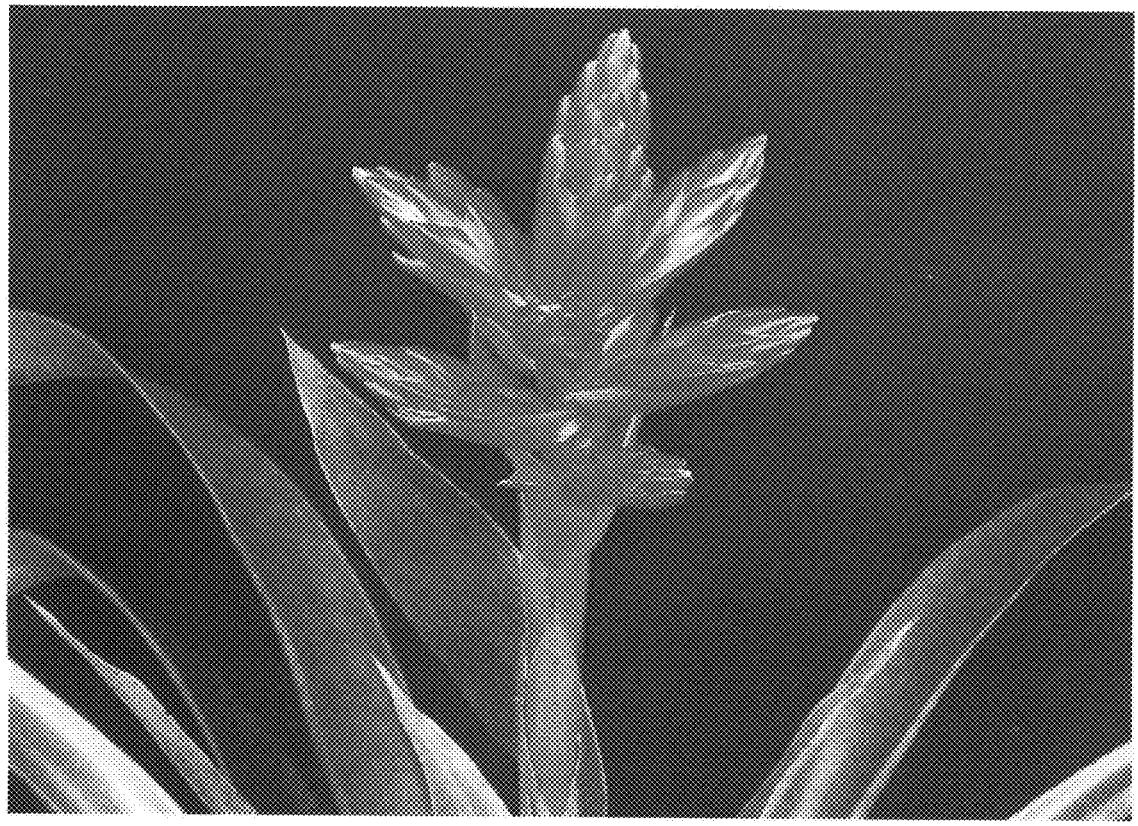
FIG. 2 shows a close-up top view perspective of the inflorescence and top bracts produced by a typical potted, flowering plant of 'AROSA', at 15 months of age in a 12 cm pot.

'AROSA' has not been tested and observed under all possible environmental conditions. The phenotype of the new cultivar may vary with variations in environment such as temperature, light intensity, frequency of fertilization, composition of fertilizer, acetylene treatment, day length and humidity, without any change in the genotype of the plant.

For example, substantial differences in plant height and diameter, number of leaves, can result depending on the size of the plant at the time that flowering is induced by acetylene treatment. Since treatment with acetylene to induce flowering disrupts normal watering and fertilization regimens, acetylene treatment of relatively smaller plants adversely affects the growth of the plant.

The aforementioned photographs, together with the following observations, measurements and values describe the new *Guzmania* 'AROSA' as grown in a greenhouse in Assendelft, The Netherlands, under conditions which closely approximate those generally used in commercial practice. Plants of 'AROSA' were grown in a greenhouse with day temperatures ranging from 20° C. to 28° C. and night temperatures ranging from 18° C. to 23° C. No artificial lighting or photoperiodic treatments were conducted, but plants of 'AROSA' are forced into flowering by adding acetylene. The following fertilizer is added when growing plants of 'AROSA': 1 part nitrogen, 0.6 parts phosphor, 2 parts Kalium and 0.1 parts magnesium.

Color references are made to The Royal Horticultural Society Colour Chart (R.H.S.), 2001 edition, except where general colors of ordinary significance are used. Color values were taken under daylight conditions in a greenhouse in Assendelft, The Netherlands. The age of the plants of 'AROSA' described is about 14 weeks after treatment with acetylene.

Classification:

*Botanical.*—*Guzmnania hybrida*

Parentage:

*Female Parent.*—*Guzmania* hybrid identified by code 973018393 (unpatented).

*Male Parent.*—*Guzmnania albo-rosea* inbred line identified by code 97301017 (unpatented).

Plant:

*General Appearance and Form.*—Height: About 45 cm (when flowering) Width: About 60 cm to 70 cm Shape: Funnel form rosette.

*Growth habit.*—Stemless.

*Plant Vigor.*—Good.

*Flowering Season.*—A fully grown plant can flower year round, starting 14 weeks after induction of natural light or through flowering treatment.

*Cold Tolerance.*—Frost tender. Temperatures below 5° C. may damage plants.

*Fragrance.*—None.

Foliage:

*Quantity.*—About 25 (depending on the size of the plant).

*Size of leaf.*—Length: About 50 cm (when flowering) Width: About 3.5 to 4.5 cm.

*Overall shape.*—Linear.

*Apex shape.*—Acute.

*Base shape.*—Strap-like around central axis.

*Margin.*—Entire.

*Texture* (*both surfaces*).—Smooth.

*Orientation.*—Leaf blades arch continuously from base.

*Color.*—Leaf color can vary somewhat depending on growing conditions Mature: Upper surface: Green, RHS 137A Lower surface: Yellow-green, RHS 147B Immature: Upper surface: Green, RHS 137A Lower surface: Yellow-green RHS 147B.

*Venation.*—None.

Inflorescence:

*Borne.*—Erect stalks.

*Shape.*—Compound.

*Size.*—Length: About 11 cm Diameter: About 11 cm.

*Time of Bloom.*—A fully grown plant can produce an inflorescence containing about 100 flowers (depending on the size of the plants), and can bloom the whole year starting about 14 weeks after natural induction or through treatment with acetylene.

*Duration of Bloom.*—Each flower blooms one (1) day and the total blooming of the whole inflorescence is about six (6) weeks.

*Petals.*—Number: 3 per flower Length: About 3.0 cm Width: About 0.5 cm Overall Shape: Ligulate Apex Shape: Obtuse Base Shape: Fused Color: Upper and lower surfaces: Yellow, RHS 4A.

*Sepals.*—Number: 3 per flower Length: About 2.0 cm Width: About 0.5 cm Overall Shape: Ligulate Apex Shape: Acute Base Shape: Fused Color: Translucent, red-purple, RHS 61A.

Bracts:

*Scape bracts.*—Quantity: About 12 Arrangement: Alternate Size: Length: About 5 cm (lowest) to about 7 cm (scape bracts positioned just below the primary bracts). Width: About 3.0 cm Overall shape: Lanceolate Apex shape: Acute Base shape: Fused Margin: Entire Texture: Smooth Color: Upper and lower surfaces: Red-purple, RHS 61A.

*Primary bracts.*—Quantity: About 8 Arrangement: Alternate Size: Length: About 5 cm (lowest) to about 4 cm (primary bracts become shorter closer to the top of plant) Width: About 3.5 cm to 5.0 cm Overall shape: Lanceolate Apex shape: Acute Base shape: Fused Margin: Entire Texture: Smooth Color: Upper and Lower surfaces: Red-purple, RHS 61A.

*Floral bracts.*—Disposed within the inflorescence.

Reproductive organs:

*Androecium.*—Stamen: Number: 6 per flower Length: About 3.0 cm Diameter: Less than 1.0 mm Color: Yellow-white, RHS 158A Anther: Length: About 0.5 cm Color: Grey-brown, RHS 199A Pollen: Amount: Scarce.

*Gynoecium.*—Pistil: Number: 1 per flower Length: About 3 cm Stigma: Shape: 3-parted Width: About 2.0 mm Color: Yellow-green, RHS 144A Style: Length: About 3.0 cm Color: Yellow-white, RHS 158A Ovary: Position: Superior Shape: Conical Length: About 0.8 cm Diameter: About 0.4 cm Color: Yellow-green, RHS 149D.

Seeds/fruit: Sterile hybrid, therefore, no seed or fruit produced.

Disease/pest resistance: No observations made.

Disease/pest susceptibility: No observations made.

We claim:

1. A new and distinct *Guzmania* hybrid plant named 'AROSA', substantially as illustrated and described herein.

* * * * *